US00PP30556P2

(12) United States Plant Patent
Hansen

(10) Patent No.: US PP30,556 P2
(45) Date of Patent: Jun. 4, 2019

(54) ***CLEMATIS* PLANT NAME 'STAND BY ME'**

(50) Latin Name: ***Clematis freemontii* x *Clematis integrifolia***
Varietal Denomination: Stand by Me

(71) Applicant: Hans A. Hansen, Zeeland, MI (US)

(72) Inventor: Hans A. Hansen, Zeeland, MI (US)

( * ) Notice: Subject to any disclaimer, the term of this patent is extended or adjusted under 35 U.S.C. 154(b) by 0 days.

(21) Appl. No.: 15/932,902

(22) Filed: May 17, 2018

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt

(57) ABSTRACT

The new hybrid plant of *Clematis* 'Stand by Me' with ovate foliage having a purplish bronze cast to the back of the foliage when young, violet-blue tepals producing multiple nodding flowers per node beginning late May and rebloom-ing through late summer on upright non-vining stems.

3 Drawing Sheets

Botanical denomination: *Clematis freemontii* x *Clematis integrifolia.*

Cultivar designation: 'Stand by Me'.

BACKGROUND OF THE INVENTION

The present invention relates to a new and distinct plant of bush-type *clematis*. The new plant was hybridized by the inventor at a personal garden in Waseca, Minn., USA from a cross made in June of 2008. The seed was from a selected, unnamed form sold by a perennial nursery in Clarkson, Nebr. of *Clematis fremontii* (not patented) as the female parent, times an unnamed, unreleased, blue-flowered selection of *Clematis integrifolia* (not patented), as the male parent. The new plant passed the original evaluation in summer of 2010 at a wholesale perennial nursery in Zeeland, Mich., USA and was the subject of the subsequent further evaluations. The new plant was selected from among many other seedlings growing at the same nursery in Zeeland, Mich. which met the rigorous criteria of excellent foliage and habit established as breeding goals.

'Stand by Me' has been asexually propagated since 2013 by shoot tip cuttings at the same nursery in Zeeland, Mich. The resultant asexually propagated plants have remained stable and exhibit the identical characteristics as the original plant.

No plants of *Clematis* 'Stand by Me' have been disclosed or sold, under this or any name, in this country or anywhere in the world, prior to the filing of this application, with the exception of that which may have been disclosed within one year of the filing of this application and was either derived directly or indirectly from the inventor. Such sales include sales from Walters Gardens, Inc. to nurseries comprising Plant Delights Nursery, Inc. and Proven Winners®. The owner of Plant Delights Nursery also viewed the plant on a private tour in 2013.

BRIEF SUMMARY OF THE INVENTION

'Stand by Me' differs from all other *clematis* known to the applicant. The nearest known cultivars are *Clematis* 'Center Star' U.S. Plant Pat. No. 17,010 and 'New Love' U.S. Plant Pat. No. 13,977. 'Center Star' is similar in height to the new plant, and the new plant is more floriferous, typically with four tepals per flower and the flowers face downward compared with the five tepals per flower and upward facing flowers of 'Center Star'. 'New Love' is shorter in habit and has lighter-colored, outwardly, verticillate flowers. The new plant is taller than the female parent, more floriferous and more vigorous than both the female and male parents. 'Stand by Me' produces smaller seed heads and open bell-shaped flowers and the female parent has shorter and broader foliage and larger seed heads from shorter urn-shaped flowers with lighter hue. Flowering season on the female parent is much earlier and has lighter green foliage. Foliage of the male parent is longer and narrower without the bronze on the underside, and the flowers have more narrow tepals with lighter blue hue.

The new plant, 'Stand by Me', differs from all *clematis* known to the inventor in the following combined traits:

1. The foliage is ovate and young foliage is concaved and has purplish bronze cast below and very lightly blushed above.
2. Multiple nodding flowers per node begin in late May to June with rebloom in the late summer typically having four tepals per flower.
3. Reflexed violet-blue tepals are slightly shiny on adaxial surface.
4. Plant habit is generally upright and non-vining but benefits from stakes or other nearby plants when mature.

BRIEF DESCRIPTION OF THE DRAWINGS

The photographs of the new plant demonstrate the overall appearance of trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
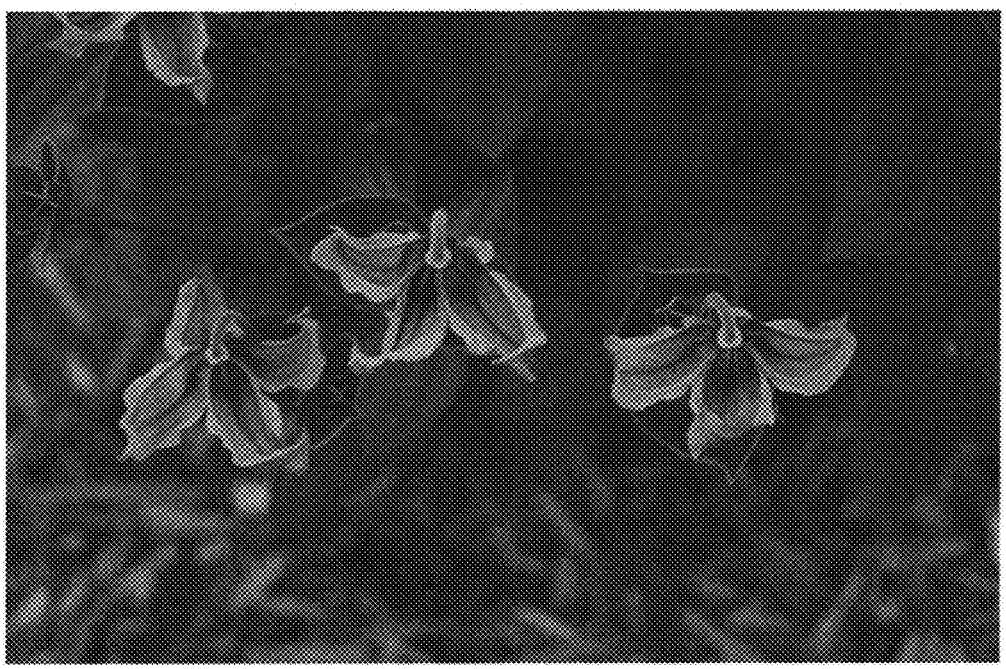
FIG. 1 a close-up of the flowers from above early in the season on a two-year-old plant.
Figure 2:
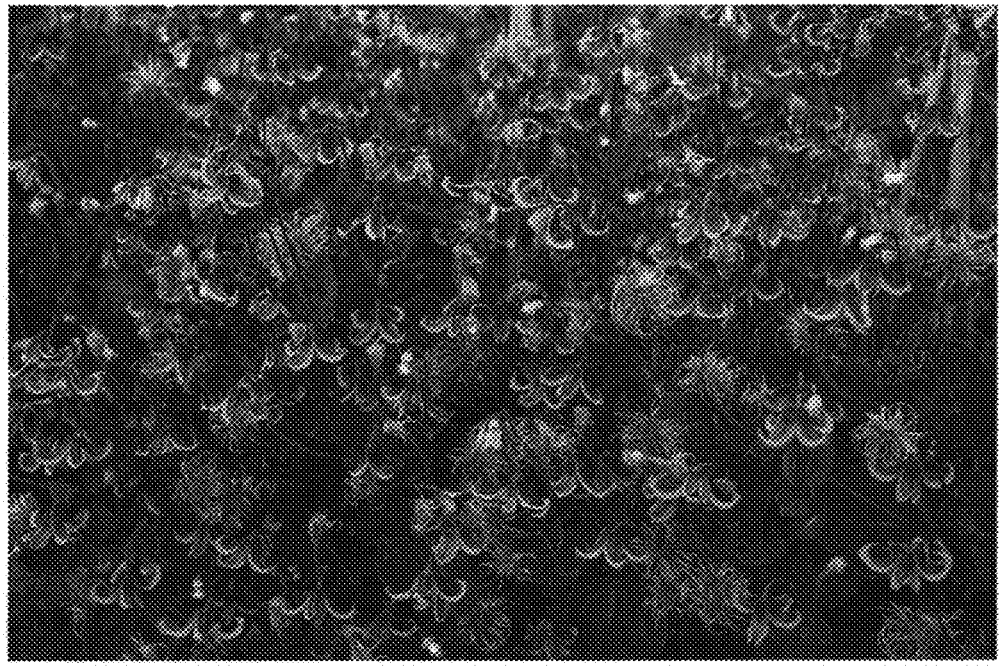
FIG. 2 shows the flowers and flower density of a five-year-old plant later in the season with some seed heads forming.
Figure 3:
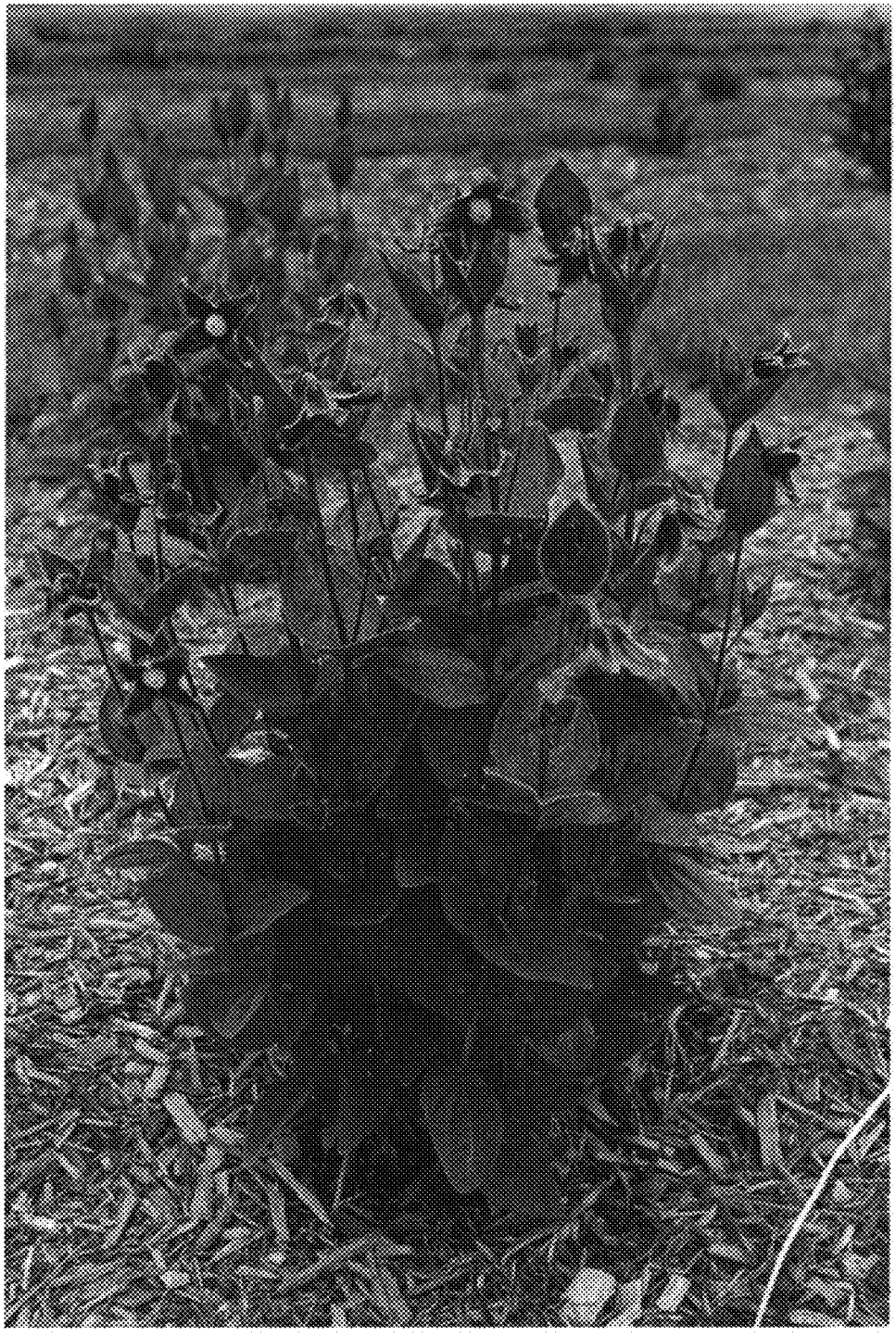
FIG. 3 shows a two-year-old plant habit early in the season as flowering is beginning.
Figure 4:
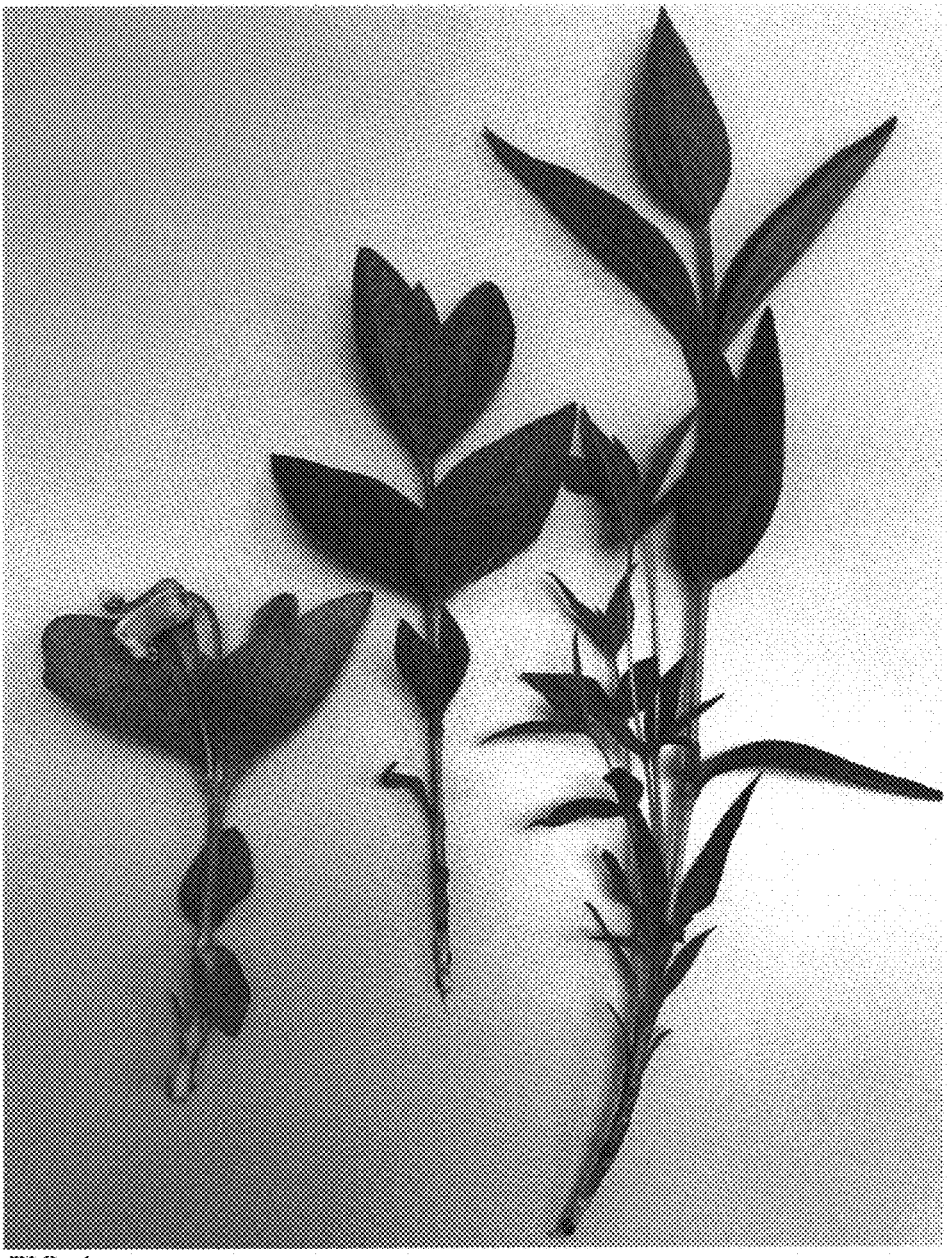
FIG. 4 shows spring stems of the new plant (middle) with female parent *C. fremontii* (left) and male parent *C. integrifolia* (right).

The following description is based on a five-year-old plant growing in a full-sun trial garden with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) an unnamed selection of *Clematis fremontii*; the male (pollen parent) was an unnamed blue-flowering selection of *Clematis integrifolia;*

Plant habit: Winter-hardy, non-vining, herbaceous perennial of semi-woody stems producing upright habit, dying to the ground each winter; to about 98.0 cm tall in flower and spreading to about 70.0 cm across about 85.0 cm above soil; foliage to about 90.0 cm tall;

Roots: Coarse, branched; tan to light brown in color depending on soil type;

Growth rate: Rapid, finishing in four-liter container in about 8 to 10 weeks from a one-year-old vernalized plant;

Stems: Angular in cross-section, six-sided with carina; glabrous proximally and pubescent distally; slightly branched; about 60 to 90 per plant; to about 90.0 cm long and 4.0 mm diameter at base; flowering in upper 30.0 to 45.0 cm;

Stem color: Proximally between RHS N167C and RHS N167D, distally nearest RHS 146B with carina nearest RHS N186C;

Internode: About 10 to 14 per stems to 5.0 mm across;

Internode color: Variable, between RHS 145A in lower light and RHS 187A in high light intensity;

Foliage: Opposite; simple; ovate; apex acute; base rounded, sessile and partially clasping; margin entire; minutely tomentose abaxial and adaxial; newly expanded foliage is concaved with young opposite leaves nearly enclosing meristem;

Leaf blade size: Variable, to about 11.5 cm long and about 6.2 cm wide in middle; average about 9.6 cm long and 5.8 cm wide;

Leaf color: Proximal mature leaves adaxial surface nearest RHS 137A, abaxial surface nearest RHS 146B; young emerging leaves adaxial surface nearest RHS 137A with very light blushing of nearest RHS 187A, abaxial surface between RHS 146A and RHS 146B with heavy blushing of RHS 187A;

Petiole: Sessile;

Veins: Palmate-penta-nerved to multi-costate; convergent;

Vein color: Adaxial mature leaves in lower stem portion nearest RHS 145C toward leaf base and toward apex nearest RHS 145B; abaxial mature leaves in lower stem between RHS 145A and RHS 145B; adaxial young leaves in upper stem nearest RHS 145C blushed with nearest RHS 183A; abaxial young leaves in upper stem between RHS 147B and RHS 147C blushed with N186C;

Inflorescence: Flowers solitary; at nodes; flowering portion about 35.0 cm long;

Flower attitude: Buds upright, flowers drooping when mature;

Flower fragrance: Faintly sweet, difficult to detect;

Flower period: Late May to June with rebloom into late summer; individual flowers remaining effective in flower for about 6 to 8 days;

Peduncle: Terete; puberulent; to about 12.5 cm long and 2.0 mm in diameter, average 8.3 cm long and 1.5 mm diameter;

Peduncle attitude: Attitude upright becoming drooping distally;

Peduncle color: Variable, nearest RHS N187A distally, proximally nearest RHS 146C with ridges of N186C, and nearest 138B on young buds;

Buds one day prior to opening: Conical with narrowly acute apex, and rounded base; glabrous with carina long tepal unions and center veins tomentose; about 24.0 mm long and 10.0 mm diameter;

Bud color: Nearest RHS N92C with carina along tepal unions nearest blend of RHS 91D and RHS 198D;

Flower: Solitary; perfect; incomplete; campanulate, cruciform; actinomorphic; about 5.2 cm across at tepal apices and 2.5 cm deep;

Flower angle: Outwardly at initial anthesis becoming drooping within 2 days of anthesis;

Tepals: Typically four in two sets; lanceolate; acute apex; cuneate to truncate base; recurved; tri-nerved with midrib and one pair of main veins; margins entire, becoming revolute; distal one-half of margin erosulate; tomentose abaxial between outer main vein and margin, glabrous and lustrous between outer main veins and midrib; adaxial glabrous and slightly lustrous; larger set average about 33.0 mm long and 15.0 mm wide in middle, smaller set average about 30.0 mm long and 11.0 mm wide in middle;

Tepal color: Adaxial center nearest RHS 90A, adaxial margin between outer main vein and margin between RHS 90D and RHS 91A; abaxial center between RHS N92D and RHS 93A, margin between outer main vein and margin between RHS 93C and RHS 93D;

Petals and sepals: Not present;

Androecium: About 60; flattened dorsa-ventrally, abaxial pubescent distal half, glabrous proximal half; total 12.0 mm long and 2.0 mm wide;

*Filaments*.—About 4.0 mm to 5.0 mm long; color nearest RHS NN155A.

*Anthers*.—Basifixed; longitudinal; ellipsoidal; toward external radius of flower; to about 3.0 mm long and 1.2 mm diameter, decreasing toward flower axis; color nearest RHS 11B.

*Pollen*.—Abundant; powdery; color nearest RHS 11C.

Gynoecium: About 60 internal to androecium; pilose with many hairs 5.0 to 6.0 mm long;

*Style*.—Terete; about 7.0 mm long and 0.2 mm diameter; pilose; color nearest RHS 155D.

*Stigma*.—Ellipsoidal; about 2.0 mm long and 0.5 mm diameter; color nearest RHS 155D.

*Torus*.—Semi-dome shaped; about 3.0 mm diameter across at base and 2.0 mm tall; color nearest RHS 160A.

Reproductive organs:

*Fruit*.—Achene: about 60 per receptacle; producing globose plumose head; initially 3.5 cm diameter, maturing to head 6.5 cm diameter.

*Seed*.—Flattened achene with style persistent as plumose tail; hairs antrorse as maturing and at nearly 90 degree angle to style when mature, extending 4.0 mm long; tail portion to 4.2 cm long, base 4.0 mm long, 3.0 mm wide and 1.0 mm thick; color maturing plumose feather stem nearest RHS 197C with hairs lighter than RHS 156D, stem base nearest RHS 160D; when mature plumose feather hairs nearest RHS 161C, stem nearest N200A and seed base between RHS 165D and RHS 165B.

*Torus*.—At maturity with seeds removed to 6.0 mm across and 3.5 mm tall; color between RHS 165B and RHS 165C.

Culture: *Clematis* 'Stand by Me' grows best in full sun with ample moisture, good drainage and mulch. The new plant is cold hardy from USDA zones 3 to at least zone 8.

Disease and pest tolerance: Pest and disease resistance and tolerance outside of that normal for *Clematis* is not known at this time.

It is claimed:

1. The new and distinct ornamental plant named *Clematis* 'Stand by Me' as herein described and illustrated.

* * * * *